United States Patent
Ullman

(10) Patent No.: US 6,244,329 B1
(45) Date of Patent: Jun. 12, 2001

(54) METHOD AND APPARATUS FOR PRODUCING CONTROLLED FREEZING OF A LIQUID

(76) Inventor: Shimon Ullman, P.O. Box 26, Rehovot 76100 (IL)

( * ) Notice: Subject to any disclaimer, the term of this patent is extended or adjusted under 35 U.S.C. 154(b) by 0 days.

(21) Appl. No.: 09/585,868

(22) Filed: Jun. 1, 2000

(51) Int. Cl.$^7$ .................................................. F25B 29/00
(52) U.S. Cl. ............................................. 165/63; 62/264
(58) Field of Search ........................... 165/61, 63; 62/66, 62/264, 340; 219/121.85; 392/407, 411, 416, 418

(56) References Cited

U.S. PATENT DOCUMENTS

| | | | | |
|---|---|---|---|---|
| 3,536,129 | * | 10/1970 | White | 165/61 |
| 5,831,249 | * | 11/1998 | Rohner et al. | 392/411 |
| 6,157,001 | * | 12/2000 | Cordrey | 392/416 |

OTHER PUBLICATIONS

"Constant Temperature Laboratory Equipment", SY–LAB GmbH, http://www.zhdanovru (web page), p. 1, 2000.
"Digital Temperature Indicator/Controller Matrix: Cryogenic Temperature Indicator and Controller Overview", http://www.scientificinstruments.com (web page), p. 1, 2000.
"Genesis Cryogenic Temperature Control System", http://www.scientificinstruments.com/genesis (web pages), pp. 1–5, 2000.
"Sylab—icecube", http://www.nikiglass.com (web page), p. 1, Sep. 8, 1999.
"Sylab—bactrac", http://www.nikiglass.com/sylab (web page), p. 1, Sep. 8, 1999.

* cited by examiner

Primary Examiner—William E. Tapolcai
(74) Attorney, Agent, or Firm—Welsh & Katz, Ltd.

(57) ABSTRACT

A system and method for producing controlled cooling of a liquid including the steps of:

removing heat from the liquid so as to cause formation of solid portions therein; and generally simultaneously with removing heat from the liquid, supplying energy to the solid portions at a frequency which is absorbed by the solid portions to a significantly greater extent than by the liquid.

66 Claims, 3 Drawing Sheets

---

GRADUALLY COOL SAMPLE BY OPERATION OF CONTROLLED-RATE FREEZER

↓

MONITOR SAMPLE TEMPERATURE DURING COOLING

↓

PRIOR TO ONSET OF SOLIDIFICATION, COMPUTER ACTUATE LASER CONTROLLER, CAUSING LASER TO IRRADIATE SAMPLE, SUCH THAT SOLID PART OF SAMPLE IS HEATED MORE THAN LIQUID PART

↓

CONTINUE CONTROLLED COOLING AND IRRADIATION OF SAMPLE UNTIL DESIRED SAMPLE TEMPERATURE IS REACHED AND MAINTAINED

METHOD AND APPARATUS FOR PRODUCING CONTROLLED FREEZING OF A LIQUID

FIELD OF THE INVENTION

The present invention relates generally to methods and apparatus for producing controlled cooling of a liquid and to liquids cooled thereby.

BACKGROUND OF THE INVENTION

The desirability of cooling liquids while preventing uncontrolled freezing thereof is well known in numerous applications, including preservation of animal and plant tissue without causing rupture of membranes therein.

It is known to cause selective lowering of the freezing temperatures of certain liquids by adding thereto certain solvents. This, however, involves contamination of the liquids which is unacceptable in many applications.

SUMMARY OF THE INVENTION

The present invention seeks to provide methods and apparatus for controlled cooling of a liquid.

There is thus provided in accordance with a preferred embodiment of the present invention a method of producing controlled freezing of a liquid including the steps of:
  removing heat from the liquid so as to cause formation of solid portions therein; and
  generally simultaneously with removing heat from the liquid, supplying energy to the solid portions at a frequency which is absorbed by the solid portions to a significantly greater extent than by the liquid.

Reference herein to "solid portions" is intended to refer not only to portions which are in fact solid prior to absorption thereof of energy, but also to portions which would be solid but for the absorption thereof of energy.

There is additionally provided in accordance with a preferred embodiment of the present invention a method of producing controlled freezing of first and second liquids, having different freezing characteristics, which are separated by a membrane, such that the membrane is not damaged as the result of freezing of at least one of the first and second liquids including:
  providing first and second liquids, having different freezing characteristics, which are separated by a membrane;
  removing heat from at least one of the first and second liquids so as to cause formation of solid portions in at least one of the first and second liquids; and
  generally simultaneously with removing heat from at least one of the first and second liquids, supplying energy to the solid portions at a frequency which is absorbed by the solid portions to a significantly greater extent than by the at least one of the first and second liquids.

Additionally in accordance with a preferred embodiment of the present invention there is provided a method of producing controlled freezing of a liquid including the steps of:
  removing heat from the liquid so as to cause formation of solid portions therein; and
  generally simultaneously with removing heat from the liquid, supplying energy to the solid portions at a frequency which is absorbed by the solid portions to a significantly greater extent than by the liquid.

Additionally in accordance with a preferred embodiment of the present invention there is provided a method of producing controlled cooling of a liquid including the steps of:
  removing heat from the liquid so as to cause formation of solid portions therein; and
  generally simultaneously with removing heat from the liquid, supplying energy to the solid portions at a frequency which is absorbed by the solid portions to a significantly greater extent than by the liquid.

Still further in accordance with a preferred embodiment of the present invention there is provided a method of producing controlled cooling of a liquid including the steps of:
  removing heat from the liquid so as to cause formation of portions therein having energy absorption characteristics different from those of the liquid; and
  generally simultaneously with removing heat from the liquid, supplying energy to the portions at a frequency which is absorbed by the portions to a significantly greater extent than by the liquid.

There is additionally provided in accordance with a preferred embodiment of the present invention a method of producing controlled cooling of a liquid including the steps of:
  removing heat from the liquid; and
  generally simultaneously with removing heat from the liquid, supplying energy thereto at a frequency which is absorbed by portions thereof to a significantly greater extent than by other portions thereof, thereby reducing the freezing temperature of the liquid.

There is also provided in accordance with a preferred embodiment of the present invention a method of producing controlled cooling of first and second liquids, having different freezing characteristics, which are separated by a membrane, such that the membrane is not damaged as the result of freezing of at least one of the first and second liquids including:
  providing first and second liquids, having different freezing characteristics, which are separated by a membrane;
  removing heat from at least one of the first and second liquids so as to cause formation of solid portions in at least one of the first and second liquids; and
  generally simultaneously with removing heat from at least one of the first and second liquids, supplying energy to the solid portions at a frequency which is absorbed by the solid portions to a significantly greater extent than by the at least one of the first and second liquids.

There is additionally provided in accordance with a preferred embodiment of the present invention a method of producing controlled freezing of a liquid containing organic molecules including the steps of:
  removing heat from the liquid so as to cause formation of solid portions therein; and
  generally simultaneously with removing heat from the liquid, supplying energy to the solid portions at a frequency which is absorbed by the solid portions to a significantly greater extent than by the liquid, whereby damage to the organic molecules is limited.

One possible example of a liquid containing organic molecules is foodstuffs, such meat or coffee, which include organic molecules within cells.

Further in accordance with a preferred embodiment of the present invention, there is provided a method of producing controlled freezing of living cells including at least first and second liquid portions, having different freezing characteristics, which are separated by at least one membrane, such that the membrane is not damaged as the result of freezing of at least one of the at least first and second liquids, the method including:

providing at least first and second liquid portions, having different freezing characteristics, which are separated by at least one membrane;

removing heat from at least one of the at least first and second liquid portions so as to cause formation of solid portions in at least one of the at least first and second liquid portions; and generally simultaneously with removing heat from at least one of the at least first and second liquid portions, supplying energy to the solid portions at a frequency which is absorbed by the solid portions to a significantly greater extent than by the at least one of the at least first and second liquid portions.

Additionally in accordance with a preferred embodiment of the present invention there is provided a method of producing controlled freezing of living tissue including a multiplicity of cells each including at least one liquid containing organic molecules including the steps of:

removing heat from the at least one liquid so as to cause formation of solid portions therein; and generally simultaneously with removing heat from the at least one liquid, supplying energy to the solid portions at a frequency which is absorbed by the solid portions to a significantly greater extent than by the at least one liquid, whereby damage to the organic molecules is limited.

There is also provided in accordance with a preferred embodiment of the present invention a method of producing controlled cooling of living tissue including a multiplicity of cells each including at least one liquid containing organic molecules including the steps of:

removing heat from the at least one liquid so as to cause formation of solid portions therein; and generally simultaneously with removing heat from the at least one liquid, supplying energy to the solid portions at a frequency which is absorbed by the solid portions to a significantly greater extent than by the at least one liquid, whereby damage to the organic molecules is limited.

There is additionally provided in accordance with a preferred embodiment of the present invention a method of producing controlled freezing of living tissue including a multiplicity of cells, each including at least one first liquid surrounded by a membrane, and at least one second liquid located outside the membrane, the method including the steps of:

removing heat from the at least one first and second liquids so as to cause formation of solid portions therein; and generally simultaneously with removing heat from the at least one first and second liquids, supplying energy to the solid portions at a frequency which is absorbed by the solid portions to a significantly greater extent than by the at least one first and second liquids, whereby damage to the membranes is limited.

Preferably, the step of supplying energy includes applying radiation at least to the solid portions.

In accordance with a preferred embodiment of the present invention, following the steps of removing heat and supplying energy, a rapid freezing step takes place followed by at least one additional repetition of the steps of removing heat, supplying energy and rapid freezing.

There is also provided in accordance with a preferred embodiment of the present invention a system for producing controlled freezing of a liquid including:

a controlled freezer, removing heat from the liquid so as to cause formation of solid portions therein; and a selective irradiator, generally simultaneously with removing heat from the liquid, supplying energy to the solid portions at a frequency which is absorbed by the solid portions to a significantly greater extent than by the liquid.

There is additionally provided in accordance with a preferred embodiment of the present invention a system for producing controlled freezing of first and second liquids, having different freezing characteristics, which are separated by a membrane, such that the membrane is not damaged as the result of freezing of at least one of the first and second liquids including:

a controlled freezer, removing heat from at least one of the first and second liquids so as to cause formation of solid portions in at least one of the first and second liquids; and a selective irradiator, operative generally simultaneously with removal of heat from at least one of the first and second liquids, supplying energy to the solid portions at a frequency which is absorbed by the solid portions to a significantly greater extent than by the at least one of the first and second liquids.

There is further provided in accordance with a preferred embodiment of the present invention a system for producing controlled cooling of a liquid including:

a controlled freezer, removing heat from the liquid so as to cause formation of solid portions therein; and a selective irradiator, generally simultaneously with removal of heat from the liquid, supplying energy to the solid portions at a frequency which is absorbed by the solid portions to a significantly greater extent than by the liquid.

Additionally in accordance with a preferred embodiment of the present invention there is provided a system for producing controlled cooling of a liquid including:

a controlled freezer, removing heat from the liquid so as to cause formation of portions therein having energy absorption characteristics different from those of the liquid; and a selective irradiator, operative generally simultaneously with removal of heat from the liquid, supplying energy to the portions at a frequency which is absorbed by the portions to a significantly greater extent than by the liquid a controlled freezer, removing heat from the liquid; and a selective irradiator, operative generally simultaneously with removal of heat from the liquid, supplying energy thereto at a frequency which is absorbed by portions thereof to a significantly greater extent than by other portions thereof, thereby reducing the freezing temperature of the liquid.

Still further in accordance with a preferred embodiment of the present invention there is provided a system for producing controlled cooling of first and second liquids which are separated by a membrane, such that the membrane is not damaged as the result of freezing of at least one of the first and second liquids including:

a controlled freezer, removing heat from at least one of the first and second liquids so as to cause formation of solid portions in at least one of the first and second liquids; and a selective irradiator, operative generally simultaneously with removal of heat from at least one of the first and second liquids, supplying energy to the solid portions at a frequency which is absorbed by the solid portions to a significantly greater extent than by the at least one of the first and second liquids.

Still further in accordance with a preferred embodiment of the present invention there is provided a system for producing controlled freezing of a liquid containing organic molecules including:

a controlled freezer, removing heat from the liquid so as to cause formation of solid portions therein; and a selective irradiator, operative generally simultaneously with removal of heat from the liquid, supplying energy to the solid portions at a frequency which is absorbed by the solid portions to a significantly greater extent than by the liquid, whereby damage to the organic molecules is limited.

Still further in accordance with a preferred embodiment of the present invention there is provided a system for producing controlled freezing of living cells including at least first and second liquid portions, having different freezing characteristics, which are separated by at least one membrane, such that the membrane is not damaged as the result of freezing of at least one of the at least first and second liquids, the system including:

a controlled freezer, removing heat from at least one of the at least first and second liquid portions so as to cause formation of solid portions in at least one of the at least first and second liquid portions; and a selective irradiator, operative generally simultaneously with removal of heat from at least one of the at least first and second liquid portions, supplying energy to the solid portions at a frequency which is absorbed by the solid portions to a significantly greater extent than by the at least one of the at least first and second liquid portions.

Additionally in accordance with a preferred embodiment of the present invention there is provided a system for producing controlled freezing of living tissue including a multiplicity of cells each including at least one liquid containing organic molecules including:

a controlled freezer, removing heat from the at least one liquid so as to cause formation of solid portions therein; and a selective irradiator, operative generally simultaneously with removal of heat from the at least one liquid, supplying energy to the solid portions at a frequency which is absorbed by the solid portions to a significantly greater extent than by the at least one liquid, whereby damage to the organic molecules is limited.

Also in accordance with a preferred embodiment of the present invention there is provided a system for producing controlled cooling of living tissue including a multiplicity of cells each including at least one liquid containing organic molecules including:

a controlled freezer, removing heat from the at least one liquid so as to cause formation of solid portions therein; and a selective irradiator, operative generally simultaneously with removal of heat from the at least one liquid, supplying energy to the solid portions at a frequency which is absorbed by the solid portions to a significantly greater extent than by the at least one liquid, whereby damage to the organic molecules is limited.

There is also provided in accordance with a preferred embodiment of the present invention there is provided a system for producing controlled freezing of living tissue including a multiplicity of cells, each including at least one first liquid surrounded by a membrane, and at least one second liquid located outside the membrane, the system including:

a controlled freezer, removing heat from the at least one first and second liquids so as to cause formation of solid portions therein; and a selective irradiator, operative generally simultaneously with removal of heat from the at least one first and second liquids, supplying energy to the solid portions at a frequency which is absorbed by the solid portions to a significantly greater extent than by the at least one first and second liquids, whereby damage to the membranes is limited.

Preferably, the selective irradiator is operative for applying radiation at least to the solid portions.

In accordance with a preferred embodiment of the present invention, following removal of heat and supplying energy, a rapid freezing takes place followed by at least one additional repetition of removing heat, supplying energy and rapid freezing.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
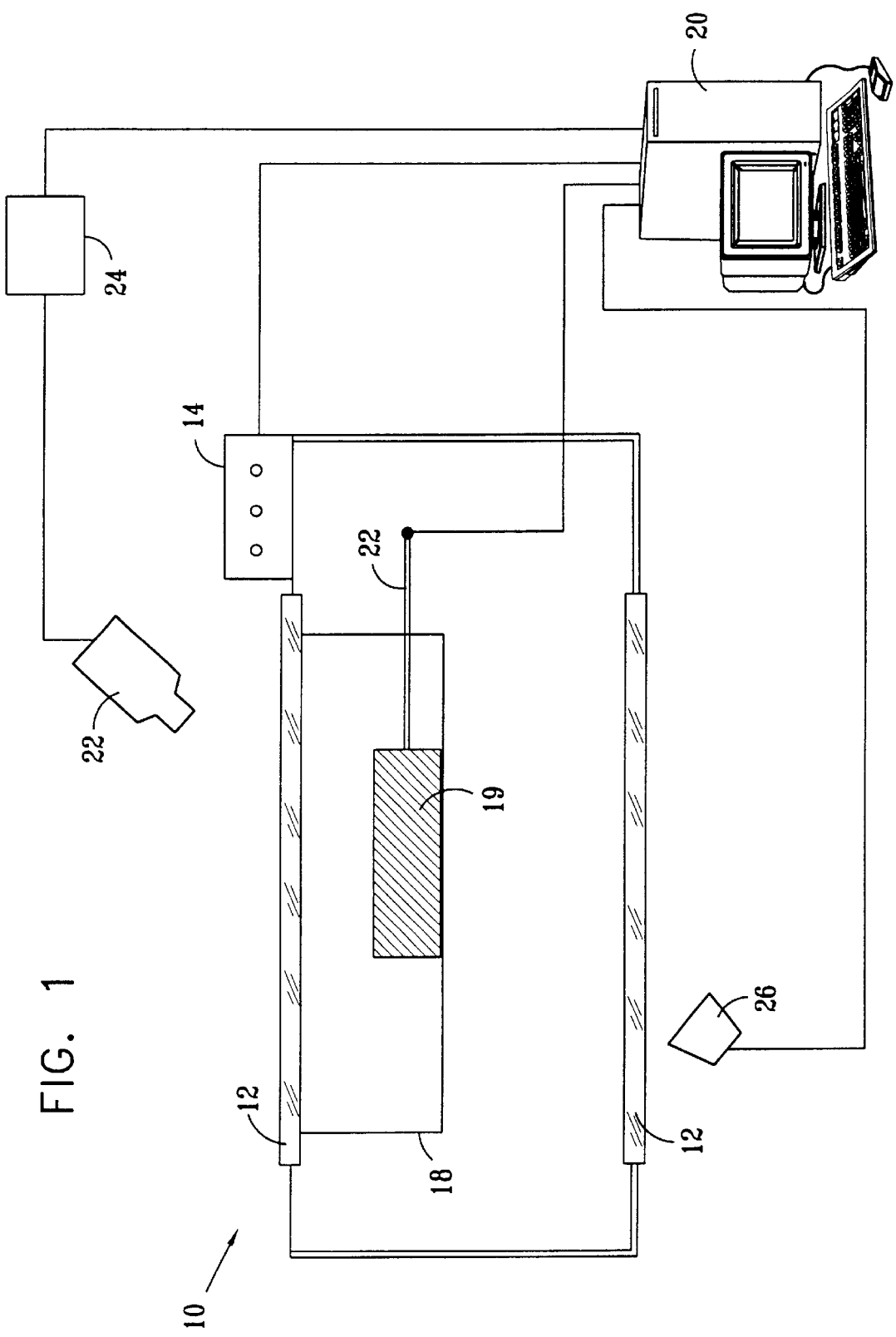
FIG. 1 is a simplified illustration of apparatus for producing controlled cooling of a liquid, constructed and operative in accordance with a preferred embodiment of the present invention.

Reference is now made to FIG. 1, which is a simplified illustration of apparatus for producing controlled cooling of a liquid, constructed and operative in accordance with a preferred embodiment of the present invention.

The apparatus of FIG. 1 preferably comprises a controlled rate freezer 10, which is commercially available under the trademark SY-LAB R from Vertiebsges. m.b.H. of Purkersdorf, Austria. The commercially available controlled rate freezer 10 is typically provided with a transparent window 12 at the top thereof. Preferably, for the purposes of the present invention, transparent windows 12 are provided on two sides thereof.

The operation of the controlled rate freezer 10 is preferably controlled by a freezer controller 14, commercially available from Scientific Instruments, Inc. of West Palm Beach, Fla. 33407, U.S.A., which measures the overall energy invested in a freezing process, without directly measuring the temperature of a sample 19 to be frozen. The functionality of the freezer controller 14 is to precisely control the rate of freezing of the sample 19.

Freezer 10 contains a cooling bath in which there is preferably provided a transparent sample holder 18, typically formed of acrylic which contains the sample 19 to be cooled.

In accordance with a preferred embodiment of the present invention a computer 20, such as a personal computer or a suitable process computer, provides operating commands to the freezer controller 14 and senses the temperature of the sample 19 in sample holder 18 by means of a temperature sensor 22, such as a platinum resistor sensor commercially available under the trademark SY-LAB R from Vertiebsges. m.b.H. of Purkersdorf, Austria.

In accordance with a preferred embodiment of the present invention, the personal computer 20 controls a laser controller 24, which, in turn, operates at least one laser 25 to irradiate the sample 19 in sample holder 18 via the transparent window 12. The laser is preferably a YAG pumped OPO operating at a wavelength of 1540 nm. It is a particular feature of the present invention that the laser irradiation is of a frequency which is absorbed to a significantly greater degree by solid sample material as opposed to liquid sample material. In this way heat is differentially supplied to the solidified portions of the sample in a controllable manner, thus limiting crystallization thereof.

In accordance with a preferred embodiment of the present invention a laser light sensor 26 may be provided in order to detect and measure the formation of solids, such as ice, in the sample. The presence of ice typically causes a drop in the intensity of the laser radiation transmitted through the sample due to the absorption of the laser light thereby.

According to an alternative embodiment of the invention, instead of laser light, other suitable types of controllable energy transmission may be employed. One example is ultrasonic energy.

Figure 2:
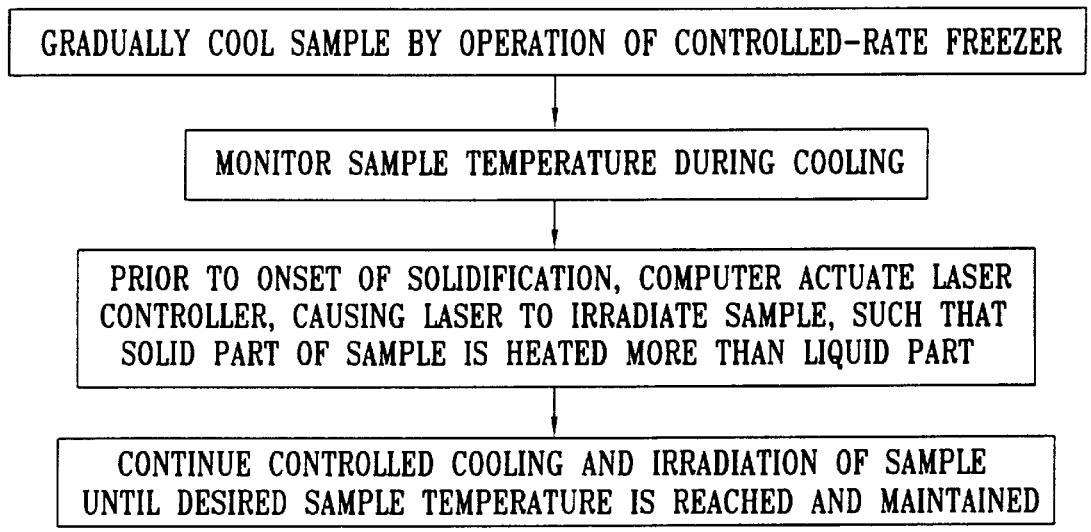
FIG. 2 is a simplified flowchart of a method of producing controlled cooling of a liquid in accordance with one embodiment of the present invention.

Reference is now made to FIG. 2, which is a simplified flowchart of a method of producing controlled cooling of a liquid in accordance with one embodiment of the present invention. As seen in FIG. 2, the liquid is gradually cooled by operation of the controlled-rate freezer and the temperature of the sample is monitored. Typically prior to the onset of solidification, the computer actuates the laser controller which causes the laser to irradiate the sample, with the result that the solid portion of the sample is heated more than is the liquid part. For example, solid ice absorbs energy at 1540 nm at a rate about three times the rate at which water absorbs energy at that wavelength. Formation of ice in the sample is also monitored, so as to limit such formation in accordance with the requirements of each application.

Cooling of the sample by the controlled rate freezer continues as does irradiation of the sample, thus increasingly cooling the sample while limiting the solidification thereof, until an desired sample temperature is reached and maintained.

According to one embodiment of the present invention, freezing of the liquid is effectively prevented, inasmuch as the radiation causes the freezing temperature of the liquid to effectively decrease by effectively preventing formation of solid portions therein.

Figure 3:
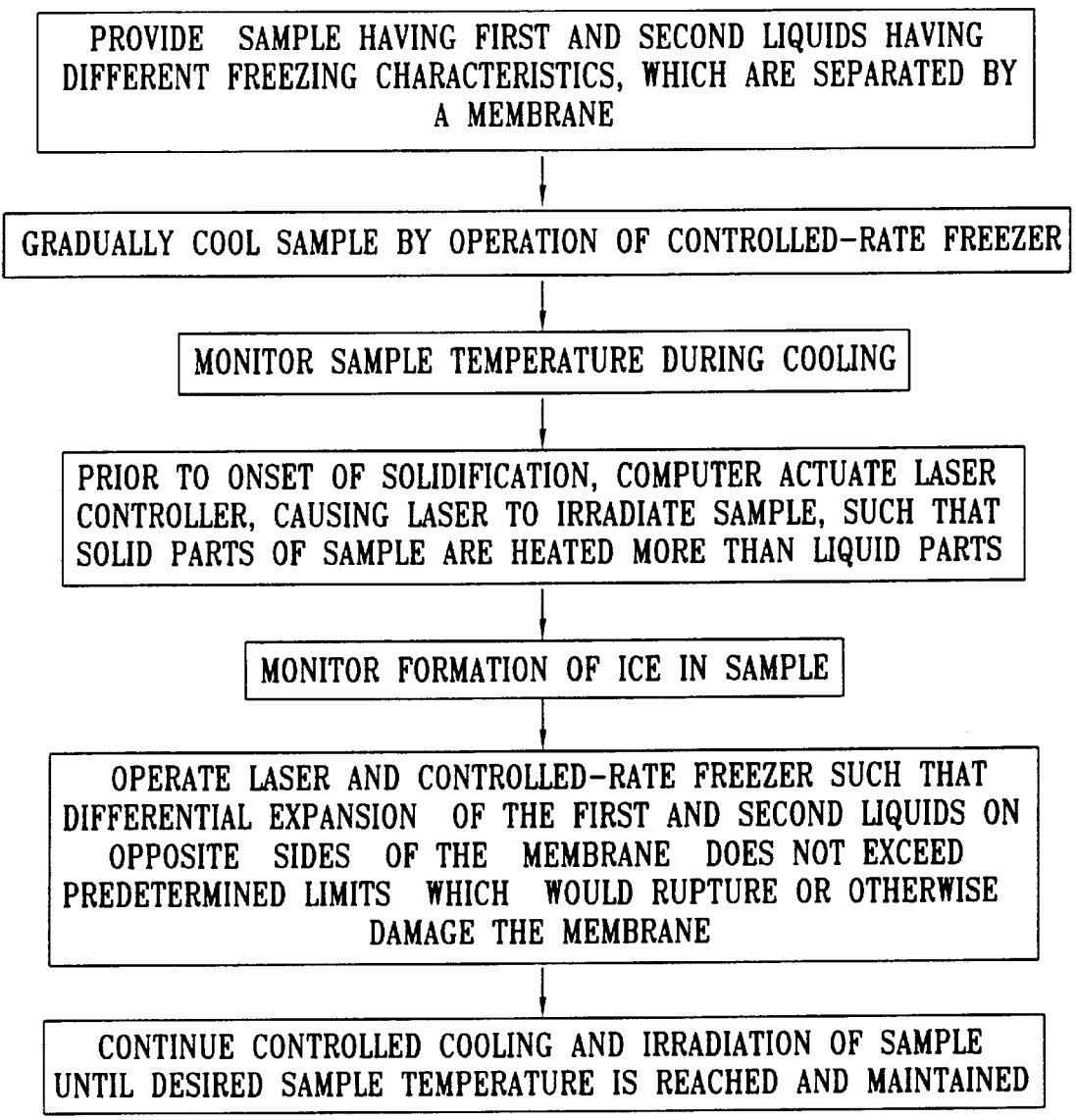
FIG. 3 is a simplified flowchart of a method of producing controlled cooling of a liquid in accordance with another embodiment of the present invention.

Reference is now made to FIG. 3, which is a simplified flowchart of a method of producing controlled cooling of a liquid in accordance with another embodiment of the present invention. In this case, the sample comprises at least first and second liquids, having different freezing characteristics, which are separated by a membrane. The purpose of the method is to freeze the sample without damaging the membrane due to different rates of freezing of the first and second liquids.

As described generally above with reference to FIG. 2, the first and second liquids are gradually cooled by operation of the controlled-rate freezer and the temperature of the sample is monitored. As solidification begins to take place, and typically even before solidification takes place, the computer actuates the laser controller which causes the laser to irradiate the sample, with the result that the solid portions of the sample is heated more than is the liquid part. For example, solid ice absorbs energy at 1540 nm at a rate about three times the rate at which water absorbs energy at that wavelength. Formation of ice in the sample is also monitored, so as to limit such formation in accordance with the requirements of each application.

Formation of ice in the sample is also monitored, so as to limit such formation in accordance with the requirements of each application. The operation of the laser is coordinated with the operation of the controlled-rate freezer such that the differential expansion of the first and second liquids on opposite sides of the membrane does not exceed predetermined limits which would rupture or otherwise damage the membrane.

It is appreciated that once a certain temperature level has been reached in this manner, the operation of the laser can be terminated, leading to rapid freezing without unacceptable differential expansion on opposite sides of the membrane. This freezing typically will involve a relatively small percentage of the total liquid in the sample and thus the above-described controlled freezing functionality will normally be repeated multiple times, in order to eventually attain a desired level of freezing of the entire sample.

It will be appreciated by persons skilled in the art that the present invention is not limited by what has been particularly shown and described hereinabove. Rather the scope of the present invention includes both combinations and subcombinations of various features described hereinabove and in the drawings as well as modifications and variations thereof which would occur to a person of ordinary skill in the art upon reading the foregoing description and which are not in the prior art.

What is claimed is:

1. A method of producing controlled freezing of a liquid including the steps of:

removing heat from the liquid so as to cause formation of solid portions therein; and generally simultaneously with removing heat from the liquid, supplying energy to the solid portions at a frequency which is absorbed by the solid portions to a significantly greater extent than by the liquid.

2. A method of producing controlled freezing of first and second liquids, having different freezing characteristics, which are separated by a membrane, such that the membrane is not damaged as the result of freezing of at least one of the first and second liquids including:

providing first and second liquids, having different freezing characteristics, which are separated by a membrane;

removing heat from at least one of the first and second liquids so as to cause formation of solid portions in at least one of the first and second liquids; and generally simultaneously with removing heat from at least one of the first and second liquids, supplying energy to the solid portions at a frequency which is absorbed by the solid portions to a significantly greater extent than by the at least one of the first and second liquids.

3. A method of producing controlled cooling of a liquid including the steps of:

removing heat from the liquid so as to cause formation of solid portions therein; and generally simultaneously with removing heat from the liquid, supplying energy to the solid portions at a frequency which is absorbed by the solid portions to a significantly greater extent than by the liquid.

4. A method of producing controlled cooling of a liquid including the steps of:

removing heat from the liquid so as to cause formation of portions therein having energy absorption characteristics different from those of the liquid; and generally simultaneously with removing heat from the liquid, supplying energy to the portions at a frequency which is absorbed by the portions to a significantly greater extent than by the liquid.

5. A method of producing controlled cooling of a liquid including the steps of:

removing heat from the liquid; and generally simultaneously with removing heat from the liquid, supplying energy thereto at a frequency which is absorbed by portions thereof to a significantly greater extent than by other portions thereof, thereby reducing the freezing temperature of the liquid.

6. A method of producing controlled cooling of first and second liquids, having different freezing characteristics, which are separated by a membrane, such that the membrane is not damaged as the result of freezing of at least one of the first and second liquids including:

providing first and second liquids, having different freezing characteristics, which are separated by a membrane;

removing heat from at least one of the first and second liquids so as to cause formation of solid portions in at least one of the first and second liquids; and generally simultaneously with removing heat from at least one of the first and second liquids, supplying energy to the solid portions at a frequency which is absorbed by the solid portions to a significantly greater extent than by the at least one of the first and second liquids.

7. A method of producing controlled freezing of a liquid containing organic molecules including the steps of:

removing heat from the liquid so as to cause formation of solid portions therein; and generally simultaneously with removing heat from the liquid, supplying energy to the solid portions at a frequency which is absorbed by the solid portions to a significantly greater extent than by the liquid, whereby damage to the organic molecules is limited.

8. A method of producing controlled freezing of living cells including at least first and second liquid portions, having different freezing characteristics, which are separated by at least one membrane, such that the membrane is not damaged as the result of freezing of at least one of the at least first and second liquids, the method including:

providing at least first and second liquid portions, having different freezing characteristics, which are separated by at least one membrane;

removing heat from at least one of the at least first and second liquid portions so as to cause formation of solid portions in at least one of the at least first and second liquid portions; and generally simultaneously with removing heat from at least one of the at least first and second liquid portions, supplying energy to the solid portions at a frequency which is absorbed by the solid portions to a significantly greater extent than by the at least one of the at least first and second liquid portions.

9. A method of producing controlled freezing of living tissue including a multiplicity of cells each including at least one liquid containing organic molecules including the steps of:

removing heat from the at least one liquid so as to cause formation of solid portions therein; and generally simultaneously with removing heat from the at least one liquid, supplying energy to the solid portions at a frequency which is absorbed by the solid portions to a significantly greater extent than by the at least one liquid, whereby damage to the organic molecules is limited.

10. A method of producing controlled cooling of living tissue including a multiplicity of cells each including at least one liquid containing organic molecules including the steps of:

removing heat from the at least one liquid so as to cause formation of solid portions therein; and generally simultaneously with removing heat from the at least one liquid, supplying energy to the solid portions at a frequency which is absorbed by the solid portions to a significantly greater extent than by the at least one liquid, whereby damage to the organic molecules is limited.

11. A method of producing controlled freezing of living tissue including a multiplicity of cells, each including at least one first liquid surrounded by a membrane, and at least one second liquid located outside the membrane, the method including the steps of:

removing heat from the at least one first and second liquids so as to cause formation of solid portions therein; and generally simultaneously with removing heat from the at least one first and second liquids, supplying energy to the solid portions at a frequency which is absorbed by the solid portions to a significantly greater extent than by the at least one first and second liquids, whereby damage to the membranes is limited.

12. A method according to claim 1 and wherein the step of supplying energy includes applying radiation at least to the solid portions.

13. A method according to claim 1 and wherein following the steps of removing heat and supplying energy, a rapid freezing step takes place followed by at least one additional repetition of the steps of removing heat, supplying energy and rapid freezing.

14. A method according to claim 2 and wherein the step of supplying energy includes applying radiation at least to the solid portions.

15. A method according to claim 2 and wherein following the steps of removing heat and supplying energy, a rapid freezing step takes place followed by at least one additional repetition of the steps of removing heat, supplying energy and rapid freezing.

16. A method according to claim 3 and wherein the step of supplying energy includes applying radiation at least to the solid portions.

17. A method according to claim 3 and wherein following the steps of removing heat and supplying energy, a rapid freezing step takes place followed by at least one additional repetition of the steps of removing heat, supplying energy and rapid freezing.

18. A method according to claim 4 and wherein the step of supplying energy includes applying radiation at least to the solid portions.

19. A method according to claim 4 and wherein following the steps of removing heat and supplying energy, a rapid freezing step takes place followed by at least one additional repetition of the steps of removing heat, supplying energy and rapid freezing.

20. A method according to claim 5 and wherein the step of supplying energy includes applying radiation at least to the solid portions.

21. A method according to claim 5 and wherein following the steps of removing heat and supplying energy, a rapid freezing step takes place followed by at least one additional repetition of the steps of removing heat, supplying energy and rapid freezing.

22. A method according to claim 6 and wherein the step of supplying energy includes applying radiation at least to the solid portions.

23. A method according to claim 6 and wherein following the steps of removing heat and supplying energy, a rapid freezing step takes place followed by at least one additional repetition of the steps of removing heat, supplying energy and rapid freezing.

24. A method according to claim 7 and wherein the step of supplying energy includes applying radiation at least to the solid portions.

25. A method according to claim 7 and wherein following the steps of removing heat and supplying energy, a rapid freezing step takes place followed by at least one additional repetition of the steps of removing heat, supplying energy and rapid freezing.

26. A method according to claim 8 and wherein the step of supplying energy includes applying radiation at least to the solid portions.

27. A method according to claim 8 and wherein following the steps of removing heat and supplying energy, a rapid freezing step takes place followed by at least one additional repetition of the steps of removing heat, supplying energy and rapid freezing.

28. A method according to claim 9 and wherein the step of supplying energy includes applying radiation at least to the solid portions.

29. A method according to claim 9 and wherein following the steps of removing heat and supplying energy, a rapid freezing step takes place followed by at least one additional repetition of the steps of removing heat, supplying energy and rapid freezing.

30. A method according to claim 10 and wherein the step of supplying energy includes applying radiation at least to the solid portions.

31. A method according to claim 10 and wherein following the steps of removing heat and supplying energy, a rapid freezing step takes place followed by at least one additional repetition of the steps of removing heat, supplying energy and rapid freezing.

32. A method according to claim 11 and wherein the step of supplying energy includes applying radiation at least to the solid portions.

33. A method according to claim 11 and wherein following the steps of removing heat and supplying energy, a rapid freezing step takes place followed by at least one additional repetition of the steps of removing heat, supplying energy and rapid freezing.

34. A system for producing controlled freezing of a liquid comprising:
 a controlled freezer, removing heat from the liquid so as to cause formation of solid portions therein; and
 a selective energizer, generally simultaneously with removing heat from the liquid, supplying energy to the solid portions at a frequency which is absorbed by the solid portions to a significantly greater extent than by the liquid.

35. A system for producing controlled freezing of first and second liquids, having different freezing characteristics, which are separated by a membrane, such that the membrane is not damaged as the result of freezing of at least one of said first and second liquids comprising:
 a controlled freezer, removing heat from at least one of the first and second liquids so as to cause formation of solid portions in at least one of said first and second liquids; and
 a selective energizer, operative generally simultaneously with removal of heat from at least one of the first and second liquids, supplying energy to the solid portions at a frequency which is absorbed by the solid portions to a significantly greater extent than by said at least one of the first and second liquids.

36. A system for producing controlled cooling of a liquid comprising:
 a controlled freezer, removing heat from the liquid so as to cause formation of solid portions therein; and
 a selective energizer, generally simultaneously with removal of heat from the liquid, supplying energy to the solid portions at a frequency which is absorbed by the solid portions to a significantly greater extent than by the liquid.

37. A system for producing controlled cooling of a liquid comprising:
 a controlled freezer, removing heat from the liquid so as to cause formation of portions therein having energy absorption characteristics different from those of the liquid; and
 a selective energizer, operative generally simultaneously with removal of heat from the liquid, supplying energy to said portions at a frequency which is absorbed by the portions to a significantly greater extent than by the liquid.

38. A system for producing controlled cooling of a liquid comprising:
 a controlled freezer, removing heat from the liquid; and
 a selective energizer, operative generally simultaneously with removal of heat from the liquid, supplying energy thereto at a frequency which is absorbed by portions thereof to a significantly greater extent than by other portions thereof, thereby reducing the freezing temperature of the liquid.

39. A system for producing controlled cooling of first and second liquids, having different freezing characteristics, which are separated by a membrane, such that the membrane is not damaged as the result of freezing of at least one of said first and second liquids comprising:
 a controlled freezer, removing heat from at least one of the first and second liquids so as to cause formation of solid portions in at least one of said first and second liquids; and
 a selective energizer, operative generally simultaneously with removal of heat from at least one of the first and second liquids, supplying energy to the solid portions at a frequency which is absorbed by the solid portions to a significantly greater extent than by said at least one of the first and second liquids.

40. A system for producing controlled freezing of a liquid containing organic molecules comprising:
 a controlled freezer, removing heat from the liquid so as to cause formation of solid portions therein; and
 a selective energizer, operative generally simultaneously with removal of heat from the liquid, supplying energy to the solid portions at a frequency which is absorbed by the solid portions to a significantly greater extent than by the liquid, whereby damage to the organic molecules is limited.

41. A system for producing controlled freezing of living cells comprising at least first and second liquid portions, having different freezing characteristics, which are separated by at least one membrane, such that the membrane is not damaged as the result of freezing of at least one of said at least first and second liquids, the system comprising:

a controlled freezer, removing heat from at least one of the at least first and second liquid portions so as to cause formation of solid portions in at least one of said at least first and second liquid portions; and a selective energizer, operative generally simultaneously with removal of heat from at least one of the at least first and second liquid portions, supplying energy to the solid portions at a frequency which is absorbed by the solid portions to a significantly greater extent than by said at least one of the at least first and second liquid portions.

42. A system for producing controlled freezing of living tissue including a multiplicity of cells each comprising at least one liquid containing organic molecules comprising:

a controlled freezer, removing heat from the at least one liquid so as to cause formation of solid portions therein; and a selective energizer, operative generally simultaneously with removal of heat from the at least one liquid, supplying energy to the solid portions at a frequency which is absorbed by the solid portions to a significantly greater extent than by the at least one liquid, whereby damage to the organic molecules is limited.

43. A system for producing controlled cooling of living tissue including a multiplicity of cells each comprising at least one liquid containing organic molecules comprising:

a controlled freezer, removing heat from the at least one liquid so as to cause formation of solid portions therein; and a selective energizer, operative generally simultaneously with removal of heat from the at least one liquid, supplying energy to the solid portions at a frequency which is absorbed by the solid portions to a significantly greater extent than by the at least one liquid, whereby damage to the organic molecules is limited.

44. A system for producing controlled freezing of living tissue including a multiplicity of cells, each comprising at least one first liquid surrounded by a membrane, and at least one second liquid located outside the membrane, the system comprising:

a controlled freezer, removing heat from the at least one first and second liquids so as to cause formation of solid portions therein; and a selective energizer, operative generally simultaneously with removal of heat from the at least one first and second liquids, supplying energy to the solid portions at a frequency which is absorbed by the solid portions to a significantly greater extent than by the at least one first and second liquids, whereby damage to the membranes is limited.

45. A system according to claim 34 and wherein the selective energizer is operative for applying radiation at least to the solid portions.

46. A system according to claim 34 and wherein the system is operative following initially removing heat and supplying energy to cause rapid freezing to take place followed by at least one additional repetition of heat removal, supplying energy and rapid freezing.

47. A system according to claim 35 and wherein the selective energizer is operative for applying radiation at least to the solid portions.

48. A system according to claim 35 and wherein the system is operative following initially removing heat and supplying energy to cause rapid freezing to take place followed by at least one additional repetition of heat removal, supplying energy and rapid freezing.

49. A system according to claim 36 and wherein the selective energizer is operative for applying radiation at least to the solid portions.

50. A system according to claim 36 and wherein the system is operative following initially removing heat and supplying energy to cause rapid freezing to take place followed by at least one additional repetition of heat removal, supplying energy and rapid freezing.

51. A system according to claim 37 and wherein the selective energizer is operative for applying radiation at least to the solid portions.

52. A system according to claim 37 and wherein the system is operative following initially removing heat and supplying energy to cause rapid freezing to take place followed by at least one additional repetition of heat removal, supplying energy and rapid freezing.

53. A system according to claim 38 and wherein the selective energizer is operative for applying radiation at least to the solid portions.

54. A system according to claim 38 and wherein the system is operative following initially removing heat and supplying energy to cause rapid freezing to take place followed by at least one additional repetition of heat removal, supplying energy and rapid freezing.

55. A system according to claim 39 and wherein the selective energizer is operative for applying radiation at least to the solid portions.

56. A system according to claim 39 and wherein the system is operative following initially removing heat and supplying energy to cause rapid freezing to take place followed by at least one additional repetition of heat removal, supplying energy and rapid freezing.

57. A system according to claim 40 and wherein the selective energizer is operative for applying radiation at least to the solid portions.

58. A system according to claim 40 and wherein the system is operative following initially removing heat and supplying energy to cause rapid freezing to take place followed by at least one additional repetition of heat removal, supplying energy and rapid freezing.

59. A system according to claim 41 and wherein the selective energizer is operative for applying radiation at least to the solid portions.

60. A system according to claim 41 and wherein the system is operative following initially removing heat and supplying energy to cause rapid freezing to take place followed by at least one additional repetition of heat removal, supplying energy and rapid freezing.

61. A system according to claim 42 and wherein the selective energizer is operative for applying radiation at least to the solid portions.

62. A system according to claim 42 and wherein the system is operative following initially removing heat and supplying energy to cause rapid freezing to take place followed by at least one additional repetition of heat removal, supplying energy and rapid freezing.

63. A system according to claim 43 and wherein the selective energizer is operative for applying radiation at least to the solid portions.

64. A system according to claim 43 and wherein the system is operative following initially removing heat and supplying energy to cause rapid freezing to take place followed by at least one additional repetition of heat removal, supplying energy and rapid freezing.

65. A system according to claim 44 and wherein the selective energizer is operative for applying radiation at least to the solid portions.

66. A system according to claim 44 and wherein the system is operative following initially removing heat and supplying energy to cause rapid freezing to take place followed by at least one additional repetition of heat removal, supplying energy and rapid freezing.

* * * * *